US009834491B2

(12) United States Patent
Lee et al.

(10) Patent No.: US 9,834,491 B2
(45) Date of Patent: Dec. 5, 2017

(54) METHOD FOR PRODUCING BIO-BASED HOMOSERINE LACTONE AND BIO-BASED ORGANIC ACID FROM O-ACYL HOMOSERINE PRODUCED BY MICROORGANISMS

(71) Applicant: CJ Cheiljedang Corporation, Seoul (KR)

(72) Inventors: Han Won Lee, Seoul (KR); Young Lyeol Yang, Gyeonggi-do (KR); So Young Kim, Gyeonggi-do (KR); Yong Uk Shin, Gyeonggi-do (KR); Jin Sook Chang, Seoul (KR); Hye Won Um, Gyeonggi-do (KR); Young Hyoung Goh, Gyeongsangnam-do (KR); Sung Hoo Jhon, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 458 days.

(21) Appl. No.: 14/219,307

(22) Filed: Mar. 19, 2014

(65) Prior Publication Data

US 2014/0296466 A1 Oct. 2, 2014

Related U.S. Application Data

(60) Provisional application No. 61/803,519, filed on Mar. 20, 2013.

(51) Int. Cl.
| | |
|---|---|
| *C07C 1/24* | (2006.01) |
| *C07D 307/22* | (2006.01) |
| *C07D 307/20* | (2006.01) |
| *C07D 307/08* | (2006.01) |
| *C07D 207/12* | (2006.01) |
| *C07C 29/09* | (2006.01) |
| *C07C 29/149* | (2006.01) |
| *C07C 29/48* | (2006.01) |

(52) U.S. Cl.
CPC ............... *C07C 1/24* (2013.01); *C07C 29/09* (2013.01); *C07C 29/149* (2013.01); *C07C 29/48* (2013.01); *C07D 207/12* (2013.01); *C07D 307/08* (2013.01); *C07D 307/20* (2013.01); *C07D 307/22* (2013.01); *C07C 2529/40* (2013.01)

(58) Field of Classification Search
None
See application file for complete search history.

(56) References Cited

U.S. PATENT DOCUMENTS

| | | | | |
|---|---|---|---|---|
| 4,301,077 A * | 11/1981 | Pesa | ......................... | B01J 23/60 549/508 |
| 5,426,195 A * | 6/1995 | Sigg | ..................... | C07D 315/00 549/266 |
| 7,863,489 B2 * | 1/2011 | Johnston | .................. | B01J 21/08 568/885 |
| 2009/0253187 A1 | 10/2009 | Shin et al. | | |
| 2010/0184164 A1 * | 7/2010 | Kim | ..................... | C12N 9/1029 435/113 |
| 2013/0273615 A1 | 10/2013 | Kim et al. | | |

FOREIGN PATENT DOCUMENTS

| | | |
|---|---|---|
| EP | 2290051 A1 | 3/2011 |
| EP | 2292783 A2 | 3/2011 |
| JP | 2001-002668 A | 1/2001 |
| JP | A2009-544309 | 12/2009 |
| JP | A2011-182778 | 9/2011 |
| JP | 2012-143183 A | 8/2012 |
| JP | 5383203 B2 | 1/2014 |
| KR | 10-2008-0011132 A | 1/2008 |
| KR | 10-2013-0006464 A | 1/2013 |
| WO | WO 2008/013432 A1 | 1/2008 |

OTHER PUBLICATIONS

Ahlers A et al. Variation of molecular weight distribution of polyethylenes obtained with homogenous Ziegler-Natta catalysts. 1988. Makromol. Chem., Rapid Commun. 9, 457-461.*
De Clercq B et al. Immobilization of multifunctional Schiff base containing ruthenium complexes on MCM-41. 2003. Applied Catalysis A: General. 345-364.*
Labinger JA et al. Selective hydroxylation of methyl groups by platinum salts in aqueous medium. Direct conversion of ethanol to ethylene glycol. 1990. Journal of American Chemical Society. vol. 112, No. 14. p. 5628-5629.*
Minh DP et al. Aqueous-phase hydrogenation of Biomass-based succinic acid to 1,4-butanediol over supported bimetallic catalysts. 2010. Top Catal. 53:1270-1273.*
Takahara I et al. Dehydration of ethanol into ethylene over solid acid catalysts. 2005. Catalysis Letters. vol. 105, Nos. 3-4. p. 249-252.*
Voelkert E et al. Determination of homoserine as the lactone. 1970. Analytical Biochemistry. 34, 131-137.*
International Search Report issued in PCT/KR2014/002467 dated Dec. 22, 2014.
EP Search Report dated Sep. 18, 2017 in EP 14886152.9.
Kase H et al., "Production of 0-ACETYL-L-Homoserine by Methionine Analog-Resistant Mutants and Regulation of Homoserine O-Transacetylase in *Corynebacterium glutamicum* " Agricultural and Biological Chemistry, Agricultural Chemical Society of Japan, JP, vol. 38, No. 10, Oct. 1974, pp. 2021-2030.

(Continued)

*Primary Examiner* — Paul J Holland
(74) *Attorney, Agent, or Firm* — Swanson & Bratschun, L.L.C.

(57) ABSTRACT

The present invention relates to a method of producing bio-based homoserine lactone and bio-based organic acid through hydrolysis of O-acyl homoserine produced by a microorganism in the presence of an acid catalyst. According to the present invention, O-acyl homoserine produced by a microorganism is used as a raw material for producing 1,4-butanediol, gamma-butyrolactone, tetrahydrofuran and the like, which are industrially highly useful. The O-acyl homoserine produced by a microorganism can substitute conventional petrochemical products, can solve environmental concerns, including the emission of pollutants and the exhaustion of natural resources, and can be continuously renewable so as not to exhaust natural resources.

20 Claims, No Drawings

(56) References Cited

OTHER PUBLICATIONS

Nagai and Flavin, "Acetylhomoserine an intermediate in the fungal biosynthesis of methionine", The Journal of Biological Chemistry, vol. 242, No. 17, Sep. 10, 1967, pp. 3884-3895.
Nagao et al., "Synthesis of O-Acyl-L-Homoserine by Liase", Journal of the American Oil Chemists' Society (JA, Springer, DE, vol. 66, No. 5, May 1989, pp. 710-713.
Natelson et al., Microchemical Journal, vol. 27, No. 4, Dec. 1982, pp. 466-483, "Specific assay for homoserine and its lactone in *Pisum sativum*. Preparation of homoserine hydroxamic acid".
Flavin M et al., Biochem. Jul. 1965 vol. 4(7), pp. 1370-1375, "Synthesis of the Succinic Ester of Homoserine, a New Intermediate in the Bacterial Biosynthesis of Methionine".
Morrison and Boyd, Organic Chemistry (vol. II) 6th Edition, 1994, pp. 981-982 (with English translation).

\* cited by examiner

SEQUENCE LISTING

<160> NUMBER OF SEQ ID NOS: 16

<210> SEQ ID NO 1
<211> LENGTH: 70
<212> TYPE: DNA
<213> ORGANISM: Artificial Sequence
<220> FEATURE:
<223> OTHER INFORMATION: primer

<400> SEQUENCE: 1
ttactctggt gcctgacatt tcaccgacaa agcccaggga acttcatcac gtgtaggctg      60
gagctgcttc      70

<210> SEQ ID NO 2
<211> LENGTH: 70
<212> TYPE: DNA
<213> ORGANISM: Artificial Sequence
<220> FEATURE:
<223> OTHER INFORMATION: primer

<400> SEQUENCE: 2 ttacccttg tttgcagccc ggaagccatt ttccaggtcg gcaattaaat catatgaata    60
tcctccttag                                                          70

<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3
aaagaatatg ccgatcggtt cgggcttagg ctccagtgcc tgttcggtgg gtgtaggctg    60
gagctgcttc                                                          70

<210> SEQ ID NO 4
<211> LENGTH: 70
<212> TYPE: DNA
<213> ORGANISM: Artificial Sequence
<220> FEATURE:
<223> OTHER INFORMATION: primer

<400> SEQUENCE: 4
agacaaccga catcgctttc aacattggcg accggagccg ggaaggcaaa catatgaata    60
tcctccttag                                                          70

<210> SEQ ID NO 5
<211> LENGTH: 71
<212> TYPE: DNA
<213> ORGANISM: Artificial Sequence
<220> FEATURE:
<223> OTHER INFORMATION: primer

<400> SEQUENCE: 5
atggctgaat ggagcggcga atatatcagc ccatacgctg agcacggcaa ggtgtaggct    60
ggagctgctt c                                                        71

<210> SEQ ID NO 6
<211> LENGTH: 65
<212> TYPE: DNA
<213> ORGANISM: Artificial Sequence
<220> FEATURE:
<223> OTHER INFORMATION: primer

<400> SEQUENCE: 6
gtattcccac gtctccgggt taatccccat ctcacgcatg atctccatat gaatatcctc    60
cttag                                                               65

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7

```
gggctttgtc ggtgaaatg                                                19
```

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8

```
actttgcgat gagcgagag                                                19
```

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9

```
aatggatcct gccgtgagcg gcgaatac                                      28
```

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10

```
agctctagac tgctgaggta cgtttcgg                                      28
```

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11

```
catatgccta cctccgaaca gaa                                           23
```

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12

```
aagctttcaa aggaaaactc cttcgt                                        26
```

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13

```
catatgccca ccctcgcgcc                                               20
```

<210> SEQ ID NO 14
<211> LENGTH: 25
<212> TYPE: DNA

```
<213> ORGANISM: Artificial Sequence
<220> FEATURE:
<223> OTHER INFORMATION: primer

<400> SEQUENCE: 14
aagcttttag atgtagaact cgatg                                         25

<210> SEQ ID NO 15
<211> LENGTH: 70
<212> TYPE: DNA
<213> ORGANISM: Artificial Sequence
<220> FEATURE:
<223> OTHER INFORMATION: primer

<400> SEQUENCE: 15
caatttcttg cgtgaagaaa acgtctttgt gatgacaact tctcgtgcgt gtgtaggctg   60
gagctgcttc                                                          70

<210> SEQ ID NO 16
<211> LENGTH: 70
<212> TYPE: DNA
<213> ORGANISM: Artificial Sequence
<220> FEATURE:
<223> OTHER INFORMATION: primer

<400> SEQUENCE: 16
aatccagcgt tggattcatg tgccgtagat cgtatggcgt gatctggtag catatgaata   60
tcctccttag                                                          70
```

METHOD FOR PRODUCING BIO-BASED HOMOSERINE LACTONE AND BIO-BASED ORGANIC ACID FROM O-ACYL HOMOSERINE PRODUCED BY MICROORGANISMS

BACKGROUND OF THE INVENTION

Field of the Invention

The present invention relates to a method for producing bio-based homoserine lactone and bio-based organic acid and their derivatives.

Description of the Prior Art

Raw material for producing industrially useful gamma-butyrolactone, 1,4-butanediol, tetrahydrofuran and the like, are mostly petrochemicals, for example, maleic anhydride, anhydrous succinic acid, acetylene, butadiene and the like.

Thus, there have recently been attempts to use environmental-friendly bio-based materials which can solve environmental concerns including the emission of pollutants and the exhaustion of natural resources and can be renewable, as substitutes for conventional petrochemicals, raw material for producing gamma-butyrolactone, 1,4-butanediol, tetrahydrofuran and the like.

For example, biodegradable polybutylene succinate can be produced by esterifying 1,4-butanediol with succinic acid and polycondensing the resulting oligomer by transesterification, and polybutylene terephthalate can be produced by esterification of 1,4-butanediol with terephthalic acid.

In recent years, succinic acid has been produced from biomass by direct microbial fermentation and has been commercially used for the production of tetrahydrofuran, 1,4-butanediol, gamma-butyrolactone and the like (Bio-Amber Inc.). US Patent Publication No. 2011/0159572 discloses a microbial organisms containing a 1,4-butanediol (BDO) pathway comprising at least one exogenous nucleic acid encoding a 1,4-butanediol (BDO) pathway enzyme expressed in a sufficient amount to produce 1,4-butanediol.

However, there were no reports yet of the use of bio-based homoserine lactone and bio-based organic acid, obtained by chemical conversion of O-acyl homoserine produced by a microorganism, as a starting material for the synthesis of industrially useful 1,4-butanediol, gamma-butyrolactone, tetrahydrofuran and the like.

SUMMARY OF THE INVENTION

It is an object of the present invention to provide the novel use of bio-based O-acyl homoserine which can solve environmental concerns including the emission of pollutants and the exhaustion of natural resources and can be renewable, as substitutes for conventional petrochemicals, raw material for producing gamma-butyrolactone, 1,4-butanediol, tetrahydrofuran and the like.

More specifically, an object of the present invention is to provide a method of synthesizing industrially useful 1,4-butanediol, gamma-butyrolactone, tetrahydrofuran and the like, using bio-based homoserine lactone and bio-based organic acid, which are obtained from O-acyl homoserine produced by a microorganism through a chemical conversion process.

An embodiment of the present invention provides a method of producing bio-based homoserine lactone and bio-based organic acid through hydrolysis of O-acyl homoserine produced by a microorganism in the presence of an acid catalyst.

Another embodiment of the present invention also provides a method of producing gamma-butyrolactone by a hydrodenitrification or deamination of the said bio-based homoserine lactone.

The present invention also provides a method for producing tetrahydrofuran, 2-pyrrolidone, N-methyl-2-pyrrolidone, N-vinyl-2-pyrrolidone, 1,4-butanediol, etc., which are derivatives of the said gamma-butyrolactone.

Another embodiment of the present invention also provides a method of producing ethanol and its derivatives as ethylene, polyethylene and monoethylene glycol etc., using organic acids produced as byproducts together with bio-based homoserine lactone through hydrolysis of acyl homoserine produced by a microorganism in the presence of an acid catalyst.

DETAILED DESCRIPTION OF THE INVENTION

A first embodiment of the present invention relates to a method of producing bio-based homoserine lactone and bio-based organic acid through hydrolysis of O-acyl homoserine produced by a microorganism in the presence of an acid catalyst.

As used herein, the term "O-acyl homoserine produced by a microorganism" refers to O-acyl homoserine produced by fermenting microorganisms.

The O-acyl homoserine could include O-acetyl-L-homoserine and O-succinyl-L-homoserine, but are not limited thereto.

In the present invention, the microorganism may belong to any species that can be genetically engineered to produce O-acyl homoserine. Examples of microorganisms that may be used in the present invention include microorganisms of *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp. and *Norcardia* sp., fungi and yeasts. Specifically, the microorganism belongs to *Corynebacteria* sp. or *Escherichia* sp. More specifically, the microorganism is an *E. coli* strain that produces O-acyl homoserine. In addition, the microorganism is specifically a strain having enhanced O-acyl homoserine productivity by transformation.

The strain having enhanced O-acetyl-L-homoserine productivity can be specifically a strain whose cystathionine gamma synthase activity, O-succinylhomoserine sulfhydrylase or O-acetylhomoserine sulfhydrylase activity may be removed or weakened.

In addition, the strain having enhanced O-acyl homoserine productivity may be a strain having enhanced O-acetyl-L-homoserine productivity.

The strain having enhanced O-acetyl-L-homoserine productivity can be specifically a strain whose homoserine O-acetyl transferase activity may be enhanced.

Moreover, the strain having enhanced O-acyl homoserine productivity may be a strain having enhanced O-succinyl-L-homoserine productivity.

The strain having enhanced O-succinyl-L-homoserine productivity can be specifically a strain whose homoserine O-succinyl transferase (MetA) activity maybe enhanced.

The embodiment of the present invention is characterized in that bio-based homoserine lactone may be produced through hydrolysis of O-acyl homoserine by a microorganism in the presence of an acid catalyst.

As used herein, the term "bio-based" means the material, for example, O-acyl homoserine is microbially produced and it is used to distinguish from a petrochemicals.

The acid catalyst can be specifically concentrated hydrochloric acid (35% or more; about 12M) or a dilute hydrochloric acid.

In the present invention, O-acyl homoserine and hydrochloric acid can be specifically used at a molar ratio of 1:1-15.

The hydrolysis reaction can be specifically performed either at 40~60° C. for 1-3 hours or under reflux for 1-3 hours.

The homoserine lactone produced by the method of the embodiment of the present invention may be deaminated to gamma-butyrolactone, which may then be used as a raw material for producing a variety of industrially highly useful materials, including tetrahydrofuran, 2-pyrrolidone, N-methyl-2-pyrrolidone, N-vinyl-2-pyrrolidone and the like.

Furthermore, the other embodiment of the present invention can be characterized in that bio-based organic acids are produced as byproducts together with the homoserine lactone.

The organic acids can include acetic acid and succinic acid, but are not limited thereto.

More specifically, the specific embodiment of the present invention is characterized in that, when O-acetyl-L-homoserine is used as O-acyl homoserine, acetic acid is produced as a byproduct together with the homoserine lactone, and when O-succinyl-L-homoserine is used as O-acyl homoserine, succinic acid is produced as a byproduct together with the homoserine lactone.

Acetic acid produced by the method of the present invention may be used as a raw material for producing a variety of industrially highly useful materials. It can be hydrogenated to ethanol according to a conventional method known in the art and the ethanol can be then dehydrated to ethylene, monoethylene glycol, ethyl acetate, diethyl ether, chloroform, iodoform, acetic acid, acetaldehyde, ethyl chloride, ethyl bromide, butadiene and the like. In addition, the ethylene can be polymerized to polymers such as polyethylene according to a method well known to those skilled in the art.

In addition, succinic acid produced by the method of the present invention can be hydrogenated to 1,4-butanediol in the presence of a catalyst, and the 1,4-butanediol may be used as a raw material for producing a variety of industrially highly useful materials and can be converted to gamma-butyrolactone, tetrahydrofuran and the like. In addition, succinic acid produced by the method of the present invention can be copolymerized with 1,4-butanediol to produce biodegradable polybutylene succinate.

The bio-based homoserine lactone produced as described above can be deaminated to gamma-butyrolactone, which may then be used as a raw material for producing a variety of industrially highly useful materials, including tetrahydrofuran, 2-pyrrolidone, N-methyl-2-pyrrolidone, N-vinyl-2-pyrrolidone, etc.

Another embodiment of the present invention relates to a method for producing gamma-butyrolactone comprising the steps of: hydrolyzing O-acyl homoserine produced by a microorganism in the presence of an acid catalyst to produce bio-based homoserine lactone and bio-based organic acid; and deaminating the homoserine lactone by hydrodenitrification using a metal catalyst and hydrogen gas to yield gamma-butyrolactone.

The step of producing bio-based homoserine lactone and bio-based organic acid from O-acyl homoserine produced by a microorganism is the same as the embodiment described above and can provide homoserine lactone by hydrolysis in the presence of an acid catalyst.

Then, the homoserine lactone can be converted to gamma-butyrolactone by hydrodenitrification using a metal catalyst and hydrogen gas. The metal catalyst used in the present invention may be a catalyst which at least one metal selected from palladium (Pd), platinum (Pt), nickel (Ni) and cobalt (Co) is supported on carbon (C) or silica, but are not limited thereto. Herein, the hydrodenitrification reaction can be specifically performed at a temperature of 100~500° C. and a hydrogen pressure of 10-100 bar.

After the reaction, the metal catalyst may be recovered for use in a subsequent reaction, and the filtrate may be concentrated and purified to yield gamma-butyrolactone.

The produced gamma-butyrolactone has a high boiling point of 204° C. It not only can be used as an intermediate for synthesizing N-methyl-2-pyrrolidone, N-vinyl-2-pyrrolidone, polyvinyl pyrrolidone and the like, but also can be used as an intermediate for aromatic compounds, antirusting agents, secondary battery electrolytic solvents, medicines or agricultural chemicals which is an important material used in various fields, including agricultural, pharmaceutical, dye, pigments, fragrances, cosmetics, petrochemicals and electronic fields.

A specific example of the present invention relates to a method for producing tetrahydrofuran, the method comprising the steps of: hydrolyzing O-acyl homoserine produced by a microorganism in the presence of an acid catalyst to produce bio-based homoserine lactone and bio-based organic acid; deaminating the homoserine lactone by hydrodenitrification using a metal catalyst and hydrogen gas, thereby producing gamma-butyrolactone; and etherifying the gamma-butyrolactone with a silane compound in the presence of a indium bromide catalyst to yield tetrahydrofuran.

The process of producing gamma-butyrolactone from O-acyl homoserine produced by a microorganism is the same as that of the embodiment described above.

The produced gamma-butyrolactone is dissolved in a solvent, and then etherified using a silane compound as a reducing agent in the presence of an indium bromide catalyst at 60~80° C. to yield tetrahydrofuran.

The solvent may be trichloromethane, benzene, toluene, acetonitrile or the like.

The silane compound is represented by the following formula 1:

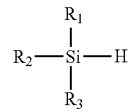

Wherein, $R_1$, $R_2$ and $R_3$ are selected from the same or different functional groups or atoms.

Specific examples of the functional groups or atoms can include a hydrogen atom, a halogen atom, an amino group, an alkyl group, a cycloalkyl group, an alkoxy group, a thioalkyl group, an alkylamino group, an aryl group, an arylamino group, a vinyl group, a siloxy group, an organosilioxy group, an organo-silyl group, a heterocyclic group, and the like. The alkyl group, the cycloalkyl group, the alkoxy group, the thioalkyl group, the alkylamino group, the aryl group, the arylamino group, the vinyl group, the siloxy group, the organo-silioxy group, the organo-silyl group and the like generally have 1-18 carbon atoms, but are not limited thereto. In addition, $R_1$, $R_2$ and $R_3$ may also have a linear, branched-chain or cyclic structure, but at least one of $R_1$, $R_2$ and $R_3$ is specifically a $C_{1-4}$ alkyl group.

In addition, in formula 1, each of $R_1$, $R_2$ and $R_3$ is specifically the same or different R or XR (wherein, R is a $C_{1-4}$ alkyl group or an aryl group, and X is a heteroatom).

The indium bromide as a catalyst is specifically used in an amount of 2-100 mass %, and specifically 5-10 mass %, based on the amount of gamma-butyrolactone, and the silane compound is specifically used in an amount equivalent to 3-5 times, specifically 3.4-4.0 times that of the gamma-butyrolactone. Also, the indium bromide is used in an amount of 1-2 moles based on 100 moles of the silane compound.

The etherification reaction is specifically carried out at a temperature of 60~80° C.

After completion of the reaction, the aqueous phase is extracted with dichloromethane (15 mL), dried over anhydrous $Na_2SO_4$, and evaporated under reduced pressure. The crude product is purified by flash column chromatography ($SiO_2$/hexane:AcOEt=99:1) to yield tetrahydrofuran.

The specific example of the present invention relates to a method for producing 2-pyrrolidone comprising the steps of: hydrolyzing O-acyl homoserine produced by a microorganism in the presence of an acid catalyst to produce bio-based homoserine lactone and bio-based organic acid; deaminating the homoserine lactone by hydrodenitrification using a metal catalyst and hydrogen gas, thereby producing gamma-butyrolactone; and producing 2-pyrrolidone from the gamma-butyrolactone in the presence of an aqueous ammonia solution at high pressure and high temperature.

The process of producing gamma-butyrolactone from O-acyl homoserine produced by a microorganism is the same as that of the embodiment described above.

The produced gamma-butyrolactone may be mixed with an aqueous ammonia solution, and then reacted in a reactor with high pressure and high temperature at a temperature of 200~375° C. and a pressure of 40-100 bar for about 1-2 hours to produce 2-pyrrolidone.

The gamma-butyrolactone and ammonia may be specifically used at a molar ratio of 1:0.5 to 1:1.5. If the molar ratio of gamma-butyrolactone used is higher than the upper limit of the above range, the production of 2-pyrrolidone will not increase, and other byproducts can be produced. For this reason, the amount of gamma-butyrolactone used is specifically within the above range.

The gamma-butyrolactone may be mixed with an aqueous ammonia solution in an anhydrous form or dissolved in water to prepare a gamma-butyrolactone solution before use.

The reaction temperature may be specifically 200~375° C. If the reaction temperature is lower than 200° C., the reaction rate will be too low, and if the reaction temperature is higher than 375° C., the concentration of byproducts other than 2-pyrrolidone will increase. For this reason, the reaction temperature is specifically within the above range.

The reaction pressure may be specifically 40-100 bar, and the reaction time may be specifically 10 minutes to 3 hours, and more specifically 1-2 hours.

Also, although 2-pyrrolidone can be produced by a batch process, it can be produced by a continuous process because it is preferable that the ammonia solution be progressively added during the process in order to reduce the production of byproducts from 4-hydroxy butyamide as an intermediate.

After completion of the reaction, water may be removed, and the residue may be extracted with chloroform. The resulting organic layer may be dried with magnesium sulfate. Magnesium sulfate may be removed by filtration, and then the filtrate is concentrated to yield 2-pyrrolidone.

Another embodiment of the present invention relates to a method for producing N-methyl-2-pyrrolidone comprising the steps of: hydrolyizng O-acyl homoserine produced by a microorganism in the presence of an acid catalyst to produce bio-based homoserine lactone and bio-based organic acid; deaminating the homoserine lactone by hydrodenitrification using a metal catalyst and hydrogen gas, thereby producing gamma-butyrolactone; and producing N-methyl-2-pyrrolidone from the gamma-butyrolactone in the presence of liquid methylamine.

The process of producing gamma-butyrolactone from O-acyl homoserine produced by a microorganism is the same as the method of the embodiment described above.

The produced gamma-butyrolactone may be mixed with liquid methylamine, and the mixture may be allowed to react at high temperature to yield N-methyl-2-pyrrolidone.

The gamma-butyrolactone and the methylamine may be used at a molar ratio of 1:1-3 (gamma-butyrolactone:methylamine).

The reaction for producing N-methyl-2-pyrrolidone may be carried out in a microwave reactor, a Parr reactor, a reactor with high pressure and high temperature or the like.

The reaction conditions can vary depending on the reactor. When a microwave reactor is used, the reaction is preformed at a temperature of 180~220° C. at atmospheric pressure for 15 minutes to 1 hour, and specifically about 30 minutes, and when a Parr reactor is used, the reaction is performed at a temperature of 200~240° C. at a pressure of 10-20 bar for 3-5 hours, and specifically about 4 hours. when a reactor with high pressure and high temperature is used, the reaction is performed at a temperature of 250~300° C. at a pressure of 50-55 bar for 30 minutes to 2 hours, and specifically about 1 hour.

After completion of the reaction, water may be removed, and the residue may be extracted with chloroform. The resulting organic layer may be dried with magnesium sulfate. Magnesium sulfate may be removed by filtration, and the filtrate is concentrated to yield N-methyl-2-pyrrolidone.

The specific example of the present invention relates to a method for producing N-vinyl-2-pyrrolidone comprising the steps of: hydrolyzing O-acyl homoserine produced by a microorganism in the presence of an acid catalyst to produce bio-based homoserine lactone and bio-based organic acid; deaminating the homoserine lactone by hydrodenitrification using a metal catalyst and hydrogen gas, thereby producing gamma-butyrolactone; dehydrating the gamma-butyrolactone in the presence of liquid ethyl alcohol amine to produce N-(2-hydroxyethyl)-2-pyrrolidone (first-stage reaction); and dehydrating the N-(2-hydroxyethyl)-2-pyrrolidone in the presence of an oxide catalyst containing an alkali metal or an alkaline earth metal and silicon to yield N-vinyl-2-pyrrolidone (second-stage reaction).

The process of producing gamma-butyrolactone from O-acyl homoserine produced by a microorganism is the same as that of the embodiment described above.

The produced gamma-butyrolactone may be dehydrated with ethyl alcohol amine in a liquid state to produce N-(2-hydroxyethyl)-2-pyrrolidone (first-stage reaction), which is then dehydrated in the presence of an oxide catalyst containing an alkali metal or an alkaline earth metal and silicon to yield N-vinyl-2-pyrrolidone (second-stage reaction).

More specifically, in the first-stage reaction, ethanol amine and water may be introduced into an autoclave under a nitrogen atmosphere, and gamma-butyrolactone may be added thereto with stirring, after which the autoclave is pressurized under 25-35 atm nitrogen pressure, and then the content in the autoclave is heated to about 200~250° C. and allowed to react for about 2 hours. In the first-stage reaction, a solution of N-(2-hydroxyethyl)-2-pyrrolidone is produced from the gamma-butyrolactone.

Then, the N-(2-hydroxyethyl)-2-pyrrolidone solution resulting from the first-stage reaction may be distilled and purified to yield N-(2-hydroxyethyl)-2-pyrrolidone.

The second-stage reaction will now be described in detail.

First, cesium carbonate as the catalyst to be used in the second-stage reaction is dissolved in water, and silicon oxide is added thereto while the solution is heated to 90° C. with stirring. The mixture is heated, concentrated, and then dried in air at 120° C. for 20 hours. The resulting solid is crushed to a size of 9-16 mesh and calcined in air at 500° C. for 2 hours, thereby preparing a catalyst having a composition of $Cs_1Si_{10}$ (excluding oxygen).

Then, the catalyst is filled into a stainless reaction tube having an inner diameter of 15 mm, and the reaction tube is placed in a reactor under high temperature (about 360° C.). Then, feed gas which is N-(2-hydroxyethyl)-2-pyrrolidone diluted with nitrogen may be supplied to the reactor at a space velocity of 200 $hr^{-1}$ and allowed to react at atmospheric pressure. After 1 hour from the initiation of the reaction, exit gas from the reactor may be captured by methanol and purified by gas chromatography to yield N-vinyl-2-pyrrolidone.

The catalyst that is used in the second-stage reaction may be an oxide represented by the following formula 2:

$$M_aSi_bX_cO_d \qquad \text{Formula 2}$$

Wherein, M is at least one element selected from alkali metals and alkaline earth metals, but are not limited thereto, Si is silicon, X is at least one element selected from among B, Al and P, and O is oxygen, but are not limited thereto. Also, if a is 1, b is 1-500, and c is 0-1, and d is determined by the values of a, b and c and the binding state of the elements.

The ratio of silicon to the alkali meal and/or the alkaline earth metal is depending on the kind of alkali meal and/or alkaline earth metal, but is typically 1-500:1 (atomic ratio), and specifically 5-200:1.

Also, X which is at least one element selected from among B, Al and P may be added optionally, the ratio of element X to the alkali meal and/or the alkaline earth metal is depending on the kind of alkali meal and/or alkaline earth metal, but is specifically 0-1:1 (atomic ratio).

The specific example of the present invention relates to a method for producing 1,4-butanediol comprising the steps of: hydrolyzing O-acyl homoserine produced by a microorganism in the presence of an acid catalyst to produce bio-based homoserine lactone and bio-based organic acid; deaminating the homoserine lactone by hydrodenitrification using a metal catalyst and hydrogen gas, thereby producing gamma-butyrolactone; and hydrogenating the gamma-butyrolactone to yield 1,4-butanediol.

The process of producing gamma-butyrolactone from O-acyl homoserine produced by a microorganism is the same as that of the embodiment described above.

The produced gamma-butyrolactone may be hydrogenated using 0.25 mol % of a ruthenium (Ru) as a catalyst and 1 mol % of an imadazole ligand in a THF solvent at 100° C. under a hydrogen gas pressure (50 bar) to produce 1,4-butanediol.

1,4-Butanediol has an annual worldwide market size of $4 billion and is used as a polymer intermediate and an industrial solvent. It is a raw material for producing polytetramethylene ether glycol that is a raw material for producing Spandex, and it reacts with a diisocyanate monomer to produce polyurethane resin. In addition, it is used for the production of polybutylene terephthalate that is a raw material for producing engineering plastic, and it may be used as an intermediate for the production of gamma-butyrolactone and the major solvent tetrahydrofuran.

Another embodiment of the present invention relates to a method for producing ethanol comprising the steps of: hydrolyzing O-acetyl-L-homoserine produced by a microorganism in the presence of an acid catalyst to produce bio-based homoserine lactone and bio-based acetic acid; and hydrogenating the acetic acid in the presence of a catalyst comprising a first metal, a siliceous support and one or more support modifiers to produce ethanol.

The process of producing bio-based homoserine lactone and bio-based acetic acid from O-acetyl-L-homoserine produced by a microorganism is the same as that of the embodiment described above.

Then, ethanol may be produced from the acetic acid by hydrogenation in the presence of a catalyst.

The catalyst may comprise a first metal, a siliceous support and one or more support modifiers.

The first metal may be selected from the group consisting of platinum, copper, iron, cobalt, nickel, ruthenium, rhodium, palladium, osmium, iridium, titanium, zinc, chromium, rhenium, molybdenum and tungsten, but are not limited thereto, and is specifically used in an amount of 0.1-25 wt % based on the total weight of the catalyst.

The siliceous support may be selected from the group consisting of silica, silica alumina and calcium metasilicate and is specifically used in an amount of 25-99 wt % based on the total weight of the catalyst. Specifically, the surface area of the siliceous support is 50 $m^2/g$-600 $m^2/g$.

The support modifiers may be selected from the group consisting of oxides and metasilicates of sodium, potassium, magnesium, calcium, scandium, yttrium and zinc, but are not limited thereto. Specifically, it is $CaSiO_3$ and may be used in an amount of 0.1-50 wt % based on the total weight of the catalyst.

The catalyst may further comprise a second metal different from the first metal. The second metal may be selected from the group consisting of copper, molybdenum, tin, chromium, iron, cobalt, vanadium, tungsten, palladium, platinum, lanthanum, cerium, manganese, ruthenium, rhenium, gold and nickel, but are not limited thereto. When the catalyst further comprises the second metal, the first metal and the second metal can be specifically used in an amount of 0.1-10 wt % based on the total weight of the catalyst.

The hydrogenation may be performed by passing hydrogen and acetic acid through the reactor at a gas hourly space velocity (GHSV) of 500 $hr^{-1}$ or more under a pressure of 10-3000 KPa at 125~350° C.

The ratio of hydrogen and acetic acid supplied may be specifically more than 2:1.

In the presence of the above-described catalyst, ethanol can be produced by the hydrogenation of acetic acid.

Ethanol produced as described above can be converted to ethylene according to a known method, for example, dehydration using concentrated sulfuric acid or gas-phase dehydration using activated alumina as a catalyst. In addition, ethanol can be converted to monoethylene glycol, ethyl acetate, diethyl ether, chloroform, iodoform, acetic acid, acetaldehyde, ethyl chloride, ethyl bromide, butadiene or the like. Further, ethylene can be polymerized to polymers such as polyethylene according to a well known polymerization method in the art.

The specific example of the present invention relates to a method for producing ethylene comprising the steps of: hydrolyzing O-acetyl-L-homoserine produced by a microorganism in the presence of an acid catalyst to produce bio-based homoserine lactone and bio-based acetic acid; hydrogenating the acetic acid in the presence of a catalyst comprising a first metal, a siliceous support and one or more support modifiers to produce ethanol; and dehydrating the ethanol in the presence of a zeolite (ZSM-5) catalyst to produce ethylene.

The process of producing ethanol from O-acetyl-L-homoserine produced by a microorganism is the same as that of the embodiment described above.

The produced ethanol may be dehydrated in the presence of a catalyst to produce ethylene. The catalyst may be specifically a zeolite (ZSM-5) catalyst, but are not limited thereto.

In a specific example of the present invention, ethanol is placed in a fixed-bed quartz reactor and allowed to react at 550° C. to produce ethylene gas.

The specific example of the present invention relates to a method for producing polyethylene comprising the steps of: hydrolyzing O-acetyl-L-homoserine produced by a microorganism in the presence of an acid catalyst to produce bio-based homoserine lactone and bio-based acetic acid; hydrogenating the acetic acid in the presence of a catalyst comprising a first metal, a siliceous support and one or more support modifiers to produce ethanol; and polymerizing the ethylene in the presence of a Ziegler-Natta catalyst to produce polyethylene.

The process of producing ethylene from O-acetyl-L-homoserine is the same as that of the embodiment described above.

The produced ethylene may be polymerized in the presence of the Ziegler-Natta catalyst to produce polyethylene.

In a specific example of the present invention, the ethylene gas may be polymerized in the presence of the Ziegler-Natta catalyst under a nitrogen gas pressure of 100 psi for 20 minutes at 50° C. to produce polyethylene.

The specific example of the present invention relates to a method for producing monoethylene glycol comprising the steps of: hydrolyzing O-acetyl-L-homoserine produced by a microorganism in the presence of an acid catalyst to produce bio-based homoseine lactone and bio-based acetic acid; hydrogenating the acetic acid in the presence of a catalyst comprising a first metal, a siliceous support and one or more support modifiers to produce ethanol; and producing monoethylene glycol from the ethanol in the presence of a $Na_2PtCl_4$ or $Na_2PtCl_6$ catalyst.

The process of producing ethanol from O-acetyl-L-homoserine is the same as that of the embodiment described above.

The produced ethanol may be converted to monoethylene glycol in the presence of a catalyst.

The catalyst used may be specifically a $Na_2PtCl_4$ or $Na_2PtCl_6$ catalyst, but are not limited thereto.

In a specific example of the present invention, ethanol may be reacted with the $Na_2PtCl_4$ or $Na_2PtCl_6$ catalyst to produce monoethylene glycol.

Another embodiment of the present invention relates to a method for producing 1,4-butanediol comprising the steps of: hydrolyzing O-succinyl-L-homoserine produced by a microorganism in the presence of an acid catalyst to produce bio-based homoserine lactone and bio-based succinic acid; and hydrogenating the succinic acid in the presence of a metal catalyst on a carbon support to produce 1,4-butanediol.

The process of producing bio-based homoserine lactone and bio-based succinic acid from O-succinyl-L-homoserine produced by a microorganism is the same as that of the embodiment described above.

The produced succinic acid may be hydrogenated in the presence of a catalyst comprising palladium (Pd), silver (Ag) and rhenium (Re) metals on a carbon support to produce 1,4-butanediol.

The catalyst may be prepared by impregnating a carbon support with a source of palladium (Pd) compound, a silver (Ag) compound and a rhenium (Re), but are not limited thereto, drying the resulting carbon support at a temperature of 150° C. or below, removing a solvent from the impregnated carbon support, and heating the dried carbon support to a temperature of 100~350° C. under reducing conditions. The prepared catalyst includes crystalline palladium having an average particle size of 10 nm or less. At least one of sources of the palladium (Pd) compound, the silver (Ag) compound and the rhenium (Re) may be a solution.

The carbon support specifically may have a BET surface area of at least 200 m$^2$/g, and specifically 500-1500 m$^2$/g. The catalyst may comprise 0.1-20 wt %, specifically 2-8 wt % of palladium (Pd), 0.1-20 wt %, specifically 1-8 wt % of silver (Ag) and 0.1-20 wt %, specifically 1-10 wt % of rhenium (Re), but are not limited thereto. The ratio of palladium (Pd) to silver (Ag) is 10:1-1:10.

The palladium compound solution is a liquid solution containing a suitable amount of a palladium compound for a catalyst comprising a required amount of palladium. The palladium compound may be a palladium compound such as palladium nitrate or chloride, carbonate, carboxylate, acetate, acetyl acetonate or amine.

The silver compound solution is a liquid solution containing a suitable amount of a silver compound for producing a catalyst comprising a required amount of silver.

The palladium compound and the silver compound would have to be reduced into metals by thermal decomposition.

The rhenium compound solution is a liquid solution containing a suitable amount of a rhenium compound for producing a catalyst comprising a required amount of rhenium. The rhenium compound may be perrhenic acid, ammonium perrhenate or alkali metal perrhenate.

A method of contacting hydrogen or a hydrogen/nitrogen mixture with the catalyst can be used to reduce the catalyst.

In the presence of the catalyst prepared as described above, succinic acid may be hydrogenated with a hydrogen-containing gas, and then purified by distillation to produce 1,4-butanediol.

The hydrogenation may be carried out by contacting hydrogen and succinic acid at the ratio of 5:1-1000:1 for 0.1 minutes to 20 hours under a hydrogen pressure of 2-400 atm at 50~350° C.

The hydrogenation can provide, in addition to 1,4-butanediol, tetrahydrofuran, gamma-butyrolactone, n-butanol, n-butyric acid, n-propanol, and mixtures thereof, but the amounts of byproducts other than 1,4-butanediol and tetrahydrofuran are very insignificant.

The separation of 1,4-butanediol from the mixture can be performed by fractional distillation, and selectivity to 1,4-butanediol is up to 73.6%.

In the step of producing 1,4-butanediol from succinic acid in the presence of a catalyst comprising palladium (Pd), silver (Ag) and rhenium (Re) metals on a carbon support by hydrogenation, tetrahydrofuran can also be produced as a byproduct.

The specific example of the present invention relates to a method for producing gamma-butyrolactone comprising the steps of: hydrolyzing O-succinyl-L-homoserine produced by a microorganism in the presence of an acid catalyst to produce bio-based homoserine lactone and bio-based succinic acid; and hydrogenating the succinic acid in the presence of a metal catalyst (Pt, Pd or Ru) on an industrial MCM-41 support to produce gamma-butyrolactone and tetrahydrofuran.

The process of producing bio-based succinic acid from O-succinyl-L-homoserine produced by a microorganism is the same as that of the embodiment described above.

The produced bio-based succinic acid may be dehydrogenated in the presence of at least one catalyst selected from a group of Platinum, Palladium and Ruthenium, to produce gamma-butyrolactone and tetrahydrofuran.

The catalyst can be prepared by impregnating a commercially available MCM-41 support with a precursor of each of platinum (Pt), palladium (Pd) and ruthenium (Ru) using a wet impregnation method, followed by drying at 100° C. for 24 hours.

Hydrogenation of the succinic acid may be performed in hydrogen flow at 450° C. under reducing conditions in the presence of the dried impregnated catalyst.

The carbon support may have a BET surface area of at least 700 $m^2$/g, and specifically 700-1000 $m^2$/g. The catalyst composition comprises 15 wt % of the precious metal precursor.

The precious metal precursor that may be used in the present invention is tetraammineplatinum (II) nitrate), palladium (II) nitrate solution, or ruthenium (III) chloride hydrate.

the specific example of the present invention relates to a method for producing gamma-butyrolactone comprising the steps of: hydrolyzing O-succinyl-L-homoserine produced by a microorganism in the presence of an acid catalyst to produce bio-based homoserine lactone and bio-based succinic acid; hydrogenating the succinic acid in the presence of a metal catalyst on a carbon support to produce 1,4-butanediol; and dehydrogenating the 1,4-butanediol in the presence of a copper-zinc-based catalyst to produce gamma-butyrolactone.

The process of producing 1,4-butanediol from O-succinyl-L-homoserine produced by a microorganism is the same as that of the embodiment described above.

The produced 1,4-butanediol may be dehydrogenated in the presence of a copper-zinc-based catalyst to produce gamma-butyrolactone.

The copper-zinc-based catalyst may be specifically Cu—ZnO—$Al_2O_3$—$ZrO_3$ produced by hydrogen reduction of plastic body (catalyst precursor) of precipitate obtained from a mixed solution of zinc nitrate, aluminum nitrate, zirconium nitrate and copper acetate and alkali hydroxide.

In the presence of the Cu—ZnO—$Al_2O_3$—$ZrO_3$ catalyst, 1,4-butanediol may be dehydrogenated in a gas phase to produce gamma-butyrolactone.

The dehydrogenation may be specifically performed at a temperature 150~400° C. at which 1,4-butanediol can be present in a gas phase. The dehydrogenation may be performed in a reactor, which includes a ceramic ring-packed vaporization layer as an upper layer and a catalyst layer as a lower layer and has a carrier gas inlet and a raw material inlet at the top and a reaction solution capture container (cooling) having a gas outlet at the bottom, but is not limited thereto.

The yield of the gamma-butyrolactone produced by the above method is 97.9%.

The specific example of the present invention relates to a method for producing tetrahydrofuran comprising the steps of: hydrolyzing O-succinyl-L-homoserine produced by a microorganism in the presence of an acid catalyst to produce bio-based homoserine lactone and bio-based succinic acid; hydrogenating the succinic acid in the presence of a metal catalyst on a carbon support to produce 1,4-butanediol; and dehydrating the 1,4-butanediol in the presence of a catalyst selected from inorganic acid, tungstic oxide supported on alumina, and iron phosphate, to produce tetrahydrofuran.

The process of producing 1,4-butanediol from O-succinyl-L-homoserine produced by a microorganism is the same as that of the embodiment described above.

The produced 1,4-butanediol may be dehydrated in the presence of a catalyst selected from inorganic acid, tungstic oxide supported on alumina and iron phosphate, to produce tetrahydrofuran, but are not limited thereto.

The inorganic acid catalyst may be an acid catalyst such as sulfuric acid or cation exchange resin. When the organic acid catalyst is used, the production of tetrahydrofuran from 1,4-butanediol may be performed by dehydrating 1,4-butanediol in a reaction column including a catalyst such as sulfuric acid or cation exchange resin under a pressure of 1-10 kg/$cm^2$ at 100~200° C. to obtain a reaction product including a mixture of water and tetrahydrofuran, introducing the reaction product into the extractive distillation column and extractive distillating continuously the reaction product under a pressure of 0.1-10 kg/$cm^2$ at 40~200° C. using 1,4-butanediol as an extraction solvent.

In the liquid phase modification, the tungstic oxide catalyst supported on alumina may be prepared in situ by heating tungstic oxide, tungstic acid ($H_2WO_4$) or either of these substances compounds with a support such as alumina, silica, or the like in the presence of the 1,4-butanediol, optionally in a hydrogen atmosphere.

When the tungstic oxide catalyst may be supported on alumina or silica on the like, a synergistic activating effect may be achieved. Thus, a catalyst prepared from a composition of 10% tungstic oxide and 90% aluminum oxide is substantially more active than one derived from tungstic oxide itself. When the tungstic oxide catalyst supported on alumina was used, the tube reactor was charged with 162 g (70 ml) of Harshaw tungsten catalyst WO 0801, ⅛ inch pellets containing 10% $WO_3$ and 90% $Al_2O_3$, and the bed was heated to 250° C. under hydrogen flow at 70 ml per minute, and then 1,4-butanediol was passed into the boiler at 36 ml per hour. When a steady state was reached, tetrahydrofuran was obtained from the condensed effluent containing only tetrahydrofur and water in 1.1 ratio.

The iron phosphate catalyst may be prepared by adding phosphoric acid or ammonium phosphate to a 1M aqueous solution of iron nitrate at a P/Fe atomic ratio of 1-1.5, stirring the mixture at 90° C. for 2 hours, and drying the stirred mixture in a dryer for 24 hours. The iron phosphate catalyst may be used alone or with a support material such as alumina, silica, titania, zeolite or activated carbon, but are not limited thereto. Specifically, the iron phosphate catalyst may be pretreated under flow of hydrogen or inert gas such as nitrogen, helium or argon at 200~400° C. before use to increase the activity of the catalyst. When the iron phosphate catalyst was used, 1,4-butanediol and 1-20 wt % of iron phosphate catalyst based on the weight of 1,4-butanediol is loaded into a liquid phase reactor, and the tetrahydrofuran was obtained from the reactor by reacting at a temperature of 150~300° C. for about 1 hour.

the specific example of the present invention relates to a method for producing N-methyl-2-pyrrolidone comprising the steps of: hydrolyzing O-succinyl-L-homoserine produced by a microorganism in the presence of an acid catalyst to produce bio-based homoserine lactone and bio-based succinic acid; hydrogenating the succinic acid in the presence of a metal catalyst on a carbon support to produce 1,4-butanediol; dehydrogenating the 1,4-butanediol in the presence of a copper-zinc-based catalyst to produce gamma-butyrolactone; and dehydrating the gamma-butyrolactone with liquid methylamine to produce N-methyl-2-pyrrolidone.

The process of producing gamma-butyrolactone from O-succinyl-L-homoserine produced by a microorganism can be the same as that of the embodiment described above.

The process of producing N-methyl-2-pyrrolidone from the produced gamma-butyrolactone is the same as that of the fifth embodiment. Specifically, N-methyl-2-pyrrolidone can be produced by mixing gamma-butyrolactone with liquid methylamine and allowing the mixture to react at high temperature.

Hereinafter, the present invention will be described in further detail with examples. It is to be understood, however, that these examples are for illustrative purposes only and are not intended to limit the scope of the present invention.

EXAMPLE 1

Construction of O-acyl Homoserine Producing Strain 1-1) Deletion of metB Gene

To deletion metB gene encoding cystathionine synthase in *E. coli* strain, FRT-one-step PCR deletion was performed (PNAS (2000) vol 97: P6640-6645). Primers of SEQ. ID. NO: 1 and NO: 2 were used for PCR using pKD3 vector including chloramphenicol marker (PNAS (2000) vol 97: P6640-6645) as a template, resulting in the construction of metB deletion cassette, named 'pKD3-ΔmetB'. PCR was performed as follows; 30 cycles of
denaturation at 94° C. for 30 seconds, annealing at 55° C., for 30 seconds, extension at 72° C. for 1 minute.

The PCR product was electroporated on 1.0% agarose gel, followed by purification of DNA obtained from 1.2 kbp band. The recovered DNA fragment was electroporated into *E. coli* (K12) W3110 transformed with pKD46 vector (PNAS (2000) vol 97: P6640-6645). Before electroporation, W3110 transformed with pKD46 was cultivated at 30° C. in LB medium containing 100 μg/L of ampicilin and 5 mM of l-arabinose until $OD_{600}$ reached 0.6. Then, the cultured strain was washed twice with sterilized distilled water and one more time with 10% glycerol. Electroporation was performed at 2500 V. The recovered strain was streaked on LB plate medium containing 25 μg/L of chloramphenichol, and was cultured at 37° C. for overnight. Then, a strain exhibiting resistance was selected.

PCR was performed by using the selected strain as a template with the same primers as the above under the same condition. The deletion of metB gene was identified by confirming the 1.2 kb sized gene on 1.0% agarose gel. The strain was then transformed with pCP20 vector (PNAS (2000) vol 97: P6640-6645) and cultured in LB medium. The final metB knock-out strain was constructed in which the size of metB gene reduced to 150 bp on 1.0% agarose gel by PCR under the same conditions. Chloramphenicol marker was confirmed to be eliminated. The constructed strain was named W3-B.

1-2) Deletion of thrB Gene

The inventors tried to increase O-succinylhomoserine synthesis from homoserine by deletion of thrB gene encoding homoserine kinase. To deletion thrB gene in the W3-B strain constructed above, FRT one step PCR deletion was performed by the same manner as described above for the deletion of metB gene.

To construct thrB deletion cassette, PCR was performed by using pKD4 vector (PNAS (2000) vol 97: P6640-6645) as a template with primers of SEQ. ID. NO: 3 and NO: 4 under the same conditions as the above 1-1. The PCR product was electroporated on 1.0% agarose gel, followed by purification of DNA obtained from 1.6 kbp band.

The recovered DNA fragment was electroporated into the W3-B strain transformed with pKD46 vector. The recovered strain was streaked on LB plate medium containing 50 μg/L of kanamycin, and cultured at 37° C. for overnight.

PCR was performed by using the selected strain as a template with primers of SEQ. ID. NO: 3 and NO: 4 under the same conditions as the above. The deletion of ThrB gene was identified by selecting the strain whose size is 1.6 kb on 1.0% agarose gel. The strain was then transformed with pCP20 vector and cultured in LB medium. The final thrB knock out strain was constructed in which the size of thrB gene reduced to 150 kb on 1.0% agarose gel by PCR under the same conditions. Kanamycin marker was confirmed to be eliminated. The constructed strain was named W3-BT.

1-3) Deletion of metJ Gene

To deletion metJ gene which is the regulator gene of meta gene involved in the O-acyl homoserine synthesis, FRT one step PCR deletion was performed by the same manner as used for the deletion of metB gene.

To construct metJ deletion cassette, PCR was performed with primers of SEQ. ID. NO: 5 and NO: 6 under the same conditions as the above 1-1.

The PCR product was electroporated on 1.0% agarose gel, followed by purification of DNA obtained from 1.2 kbp band. The recovered DNA fragment was electroporated into the W3-BT strain transformed with pKD46 vector. The recovered strain was streaked on LB plate medium containing chloramphenicol, and cultured at 37° C. for overnight. Then, a strain exhibiting resistance was selected.

PCR was performed by using the selected strain as a template with primers of SEQ. ID. NO: 7 and NO: 8 under the same conditions as the above. The deletion of metJ was identified by confirming the 1.6 kb sized gene on the 1.0% agarose gel. The strain was then transformed with pCP20 vector and cultured in LB medium. The final metJ knock out strain was constructed in which the size of metJ gene reduced to 600 kb on 1.0% agarose gel by PCR under the same conditions and the strain Chloramphenicol marker was confirmed to be eliminated. The constructed strain was named W3-BTJ.

1-4-1) Over-expression of metA Gene

To increase O-acylhomoseine synthesis, metA gene encoding homoserine O-succinyl transferase involved in the synthesis of O-succinyl homoserine from homoserine, was over-expressed.

PCR was performed by using the chromosome of *E. coli* w3110 as a template with primers of SEQ. ID. NO: 9 and NO: 10 as follows; 25 cycles of denaturation at 94° C. for 30 seconds, annealing at 55 for 30 seconds, extension at 72° C. for 2 minutes.

The PCR product was electroporated on 1.0% agarose gel, followed by purification of DNA obtained from 1.2 kbp band. The recovered DNA fragment was ligated to another DNA fragment obtained from pCL1920 vector by digesting with SmaI. *E. coli* was transformed with the ligated vector, which was then cultured in LB medium containing 50 μg/L of spectinomycin, followed by selection. The vector constructed thereby was named pMetA-CL. W3-BTJ strain was transformed with the said vector. The constructed strain was named W3-BTJ/pMetA-CL and the increase of O-succinylhomoserine level therein was observed.

As another method to increase metA gene expression, metA gene was ligated to pCL1920 vector with CJ1 promoter (CJ, Korea, Korean Patent Registration No. 10-0620092) and E. coli was transformed with the ligated vector, which was then cultured in LB medium containing 50 μg/L of spectinomycin, followed by selection. The vector constructed thereby was named pCJ-MetA-CL. W3-BTJ strain was transformed with the said vector. The constructed strain was named W3-BTJ/pCJ-MetA-CL and the increase of O-succinylhomoserine level therein was observed.

1-4-2) Over-expression of metX Gene

To synthesize O-acetylhomoserine, metX gene encoding homoserine O-acetyl transferase involved in the synthesis of O-acetylhomoserine from homoserine, was over-expressed.

PCR was performed by using the chromosome of *Leptospira meyeri* as a template with primers of SEQ. ID. NO: 11 and NO: 12 as follows under the same conditions as the above 1-4-1.

The PCR product was electroporated on 1.0% agarose gel, followed by purification of DNA obtained from 1.1 kbp band. The recovered DNA fragment was ligated to pCL1920 vector with CJ1 promoter. E. coli was transformed with the ligated vector, which was then cultured in LB medium containing 50 μg/L of spectinomycin, followed by selection. The vector constructed thereby was named pCJ1-MetXlme-CL. W3-BTJ strain was transformed with the said vector. The constructed strain was named W3-BTJ/pCJ-MetXlme-CL and the increase of O-acetylhomoserine level therein was observed.

Another method to over-express metX gene, PCR was performed by using the chromosome of *Corynebacterium* as a template with primers of SEQ. ID. NO: 13 and NO: 14 under the same conditions as the above 1-4-1.

The PCR product was electroporated on 1.0% agarose gel, followed by purification of DNA. The recovered DNA fragment was ligated to pCL1920 vector with CJ1 promoter. E. coli was transformed with the ligated vector, which was then cultured in LB medium containing 50 μg/L of spectinomycin, followed by selection. The vector constructed thereby was named pCJ-MetXcgl-CL. W3-BTJ strain was transformed with the said vector. The constructed strain was named W3-BTJ/pCJ-MetXcgl-CL and the increase of O-acetylhomoserine level therein was observed.

1-4-3) Deletion of metA Gene

To increase the production of O-acetylhomoserine, metA gene encoding homoserine O-succinyl transferase was deleted in W3-BTJ strain. Introduction of only metX gene into W3-BTJ resulted in the accumulation of O-succinylhomoserine, so that it was expected deletion of metA gene would result in the promotion of the accumulation of O-acetylhomoserine (see, Table 3). To deletion metA gene, FRT one step PCR deletion was performed.

To construct metA deletion cassette, PCR was performed with primers of SEQ. ID. NO: 15 and NO: 16 under the same conditions as the above 1-1.

The PCR product was electroporated on 1.0% agarose gel, followed by purification of DNA obtained from 1.2 kbp band. The recovered DNA fragment was electroporated into the E. coli W3-BTJ strain transformed with pKD46 vector. The recovered strain was streaked on LB plate medium containing chloramphenicol, and cultured at 37° C. for overnight. Then, a strain exhibiting resistance was selected.

PCR was performed by using the selected strain as a template with primers of SEQ. ID. NO: 15 and NO: 16 under the same conditions as the above. The deletion of metA gene was identified by confirming 1.1 kb sized gene on 1.0% agarose gel. The strain was then transformed with pCP20 vector and cultured in LB medium. The final metA knock out strain was constructed in which the size of metA gene reduced to 100 kb on 1.0% agarose gel by PCR under the same conditions. Chloramphenicol marker was confirmed to be eliminated. The constructed strain was named W3-BTJA. The W3-BTJA strain was transformed with the pCJ-MeTX-lme-CL vector and the resultant strain was named W3-BTJA/pCJ-MetX-CL. The strain was cultured by the same manner as described above and as a result the accumulation of O-succinylhomoserine was not observed, but the production of O-acetylhomoserine was significantly, approximately 20% increased, compared with W3-BTJ.

1-5) Transformation of L-threonine Producing Strain

O-acyl homoserine producing strains were constructed by the same manner as described in Examples <1-1> to <1-3> using E. coli CJM002 (KCCM-10568), the strain producing L-threonine, free from the requirement for methionine. The constructed strains were named CJM-BTJ.

In addition, CJM-BTJ/pMetA-CL (accession number: KCCM-10767) and CJM-BTJ/pCJ-MetA-CL (accession number: KCCM-10872) were constructed in the same manner as Example 1-4-1. The CJMBTJ/pMetA-CL and CJM-BTJ pCJ-MetA-CL strains were O-succinyl homoserine-producing E. coli strains transformed so as to have deletions of metB, thrB and metJ and over-express metA. However, the CJM-BTJpCJ-MetA-CL strain was constructed using the CJ1 promoter in order to over-express metA, unlike the CJM-BTJ/pMetA-CL strain (accession number: KCCM-10767).

The metX gene overexpressed, metA gene knock-out strain was also constructed by the same manner as described in <1-4-2> and <1-4-3> using the CJM-BTJ strain and the resultant strain was named CJM-BTJA pCJMetX-CL (accession number: KCCM-10873). This strain is an E. coli strain transformed so as to have deletions of metB, thrB, metJ and metA and overexpress metX, and it has improved ability to produce O-acetyl-L-homoserine.

EXAMPLE 2

Fermentation for the Production of O-acyl Homoserine

To investigate the O-acyl homoserine production capacity of the strain constructed in Example 1, Erlenmeyer flask culture was performed. The compositions of production medium are shown in Table 1 below.

W3-BTJ, CJM-BTJ and W3-BTJ and CJM-BTJ transformed with metA and metX expression vector were cultured on LB plate media containing spectinomycin at 31° C. for overnight. A single colony was inoculated in 3 ml of LB medium containing spectinomycin, and was cultured at 31° C. for 5 hours. The culture solution was 200 fold diluted in 250 ml Erlenmeyer flask containing 25 ml of medium producing methionine precursor, followed by culture at 31° C., 200 rpm for 64 hours. HPLC was performed to compare the O-acyl homoserine production capacity (see, Table 2 and Table 3).

As a result, O-acyl homoserine capacity was significantly increased in when it was produced using the strain producing L-threonine, free from the requirement for methionine.

TABLE 1

Flask medium compositions for O-acyl homoserine production

| Composition | Concentration (per liter) |
| --- | --- |
| Glucose | 40 g |
| Ammonium sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.15 g |
| Threonine | 0.15 g |

TABLE 2

O-succinyl-L-homoserine production by flask culture

| Strain | OD | Glucose consumption (g/L) | O-succinyl-L-homoserine (g/L) |
| --- | --- | --- | --- |
| W3-BTJ | 10 | 40 | 0.3 |
| W3-BTJ/pMetA-CL | 12 | 40 | 1.2 |
| W3-BTJ/pCJ-MetA-CL | 12 | 40 | 1.8 |
| CJM-BTJ | 5.0 | 33 | 0.6 |
| CJM-BTJ/pMetA-CL (KCCM-10767) | 6.0 | 36 | 5.2 |
| CJM-BTJ/pCJ-MetA-CL (KCCM-10872) | 6.0 | 40 | 10.1 |

TABLE 3

O-acetyl-L-homoserine production by flask culture

| | OD | Glucose consumption (g/L) | O-acetyl-L-homoserine (g/L) |
| --- | --- | --- | --- |
| W3-BTJ | 10 | 40 | 0 |
| W3-BTJ/pCJ-MetXlme-CL | 12 | 40 | 1.5 |
| W3-BTJ/pCJ-MetXcgl-CL | 12 | 40 | 1.4 |
| W3-BTJA/pCJ-MetXlme | 11 | 40 | 1.8 |
| CJM-BTJ | 5.0 | 33 | 0 |
| CJM-BTJ/pCJ-MetXlme-CL | 5.5 | 40 | 4.8 |
| CJM-BTJ/pCJ-MetXcgl-CL | 6.0 | 36 | 4.6 |
| CJM-BTJA/pCJ-MetX-CL (KCCM-10873) | 5.8 | 40 | 6.5 |

For mass production of O-acyl homoserine, 5-L fermentor culture was performed. The compositions of the medium used in the fermentor are shown in Table 4 below.

CJM-BTJ/pCJ-metA-CL (accession number: KCCM-10872) or CJM-BTJA/pCJ-metX-CL (accession number: KCCM-10873) was inoculated in LB medium containing spectinomycin, followed by culture at 31° C. for overnight.

Then, a single colony was inoculated in 10 ml LB medium containing spectinomycin, which was cultured at 31° C. for 5 hours. The culture solution was 100 fold diluted in 1000 ml Erlenmeyer flask containing 200 ml of O-acyl homoserine seed medium, followed by culture at 31° C., 200 rpm for 3-10 hours. The culture solution was inoculated in a 5 L fermentor, followed by further culture for 50-100 hours by fed-batch fermentation. The O-acyl homoserine concentration in the fermented solution was analyzed by HPLC and the results are shown in Table 5.

TABLE 4

Fermentor medium compositions for O-acyl homoserine production

| Composition | Seed medium | Main medium | Feed medium |
| --- | --- | --- | --- |
| Glucose (g/L) | 10.1 | 40 | 600 |
| $MgSO_4 \cdot 7H_2O$ (g/L) | 0.5 | 4.2 | |
| Yeast extract (g/L) | 10 | 3.2 | |
| $KH_2PO_4$ | 3 | 3 | 8 |
| Ammonium sulfate (g/L) | | 6.3 | |
| $NH_4Cl$ (g/L) | 1 | | |
| NaCl (g/L) | 0.5 | | |
| $Na_2HPO4 \cdot 12H_2O$ (g/L) | 5.07 | | |
| DL-methionine (g/L) | | 0.5 | 0.5 |
| L-isoleucine (g/L) | 0.05 | 0.5 | 0.5 |
| L-threonine (g/L) | | 0.5 | 0.5 |

TABLE 5

O-acyl homoserine production in a fermentor

| Strain | O-succinyl-L-homoserine (g/L) | O-acetyl-L-homoserine (g/L) |
| --- | --- | --- |
| CJM-BTJ/pCJ-MetA-CL (KCCM-10872) | >80 | 0 |
| CJM-BTJA/pCJ-MetX-CL (KCCM-10873) | 0 | >55 |

EXAMPLE 3

Synthesis of Homoserine Lactone and Organic Acid from O-acyl Homoserine

The following Examples were performed using O-acyl homoserines, especially O-acetyl-L-homoserine and O-succinyl-L-homoserine, produced by microorganisms in Example 2.

3-1) Synthesis of Homoserine Lactone and Acetic Acid from O-acetyl-L-homoserine (1) 2 g (12.4 mmol) of O-acetyl-L-homoserine was completely dissolved in 10 ml (120 mmol, 9.7 equivalents) of concentrated hydrochloric acid, and the solution was allowed to react at 50° C. for 2 hours, followed by removal of the hydrochloric acid, thereby obtaining 1.7 g (12.3 mmol) of homoserine lactone hydrochloride (purity: 99%).

$^1$H NMR (300 MHz, DMSO) δ 8.83 (2H, brs), 4.46 (1H, t, J=8.8 Hz), 4.36-4.24 (2H, m), 2.61-2.51 (1H, m), 2.30 (1H, t, J=10.3 Hz)

$^1$H NMR (300 MHz, $D_2O$) δ 4.36 (1H, t, J=9.0 Hz), 4.29 (2H, q, J=9.0 Hz), 2.69-2.60 (1H, m), 2.36-2.21 (1H, m)

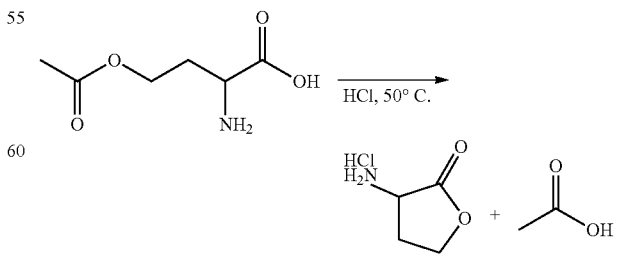

(2) 2 g (12.4 mmol) of O-acetyl-L-homoserine was completely dissolved in a mixture of 1.13 ml (13.6 mmol, 9.7 equivalents) (1.24 M) of concentrated hydrochloric acid and 10 ml of water, and the solution was allowed to react under reflux for 2 hours, followed by removal of the hydrochloric acid, thereby obtaining 1.7 g (12.3 mmol) of homoserine lactone chloride (purity: 99%).

$^1$H NMR (300 MHz, DMSO) δ 8.83 (2H, brs), 4.46 (1H, t, J=8.8 Hz), 4.36-4.24 (2H, m), 2.61-2.51 (1H, m), 2.30 (1H, t, J=10.3 Hz)

$^1$H NMR (300 MHz, D$_2$O) δ 4.36 (1H, t, J=9.0 Hz), 4.29 (2H, q, J=9.0 Hz), 2.69-2.60 (1H, m), 2.36-2.21 (1H, m)

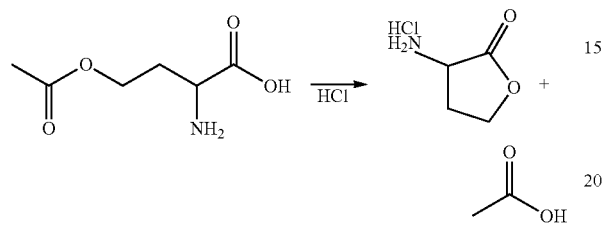

(3) 10 g (62.1 mmol) of O-acetyl-L-homoserine was completely dissolved in 50 ml (1.24 M) of water and 5.7 ml (68.3 mmol, 1.1 equivalents) of concentrated hydrochloric acid, and the solution was allowed to react under reflux for 2 hours, followed by removal of the solvent, thereby obtaining 8.5 g (61.8 mmol) of homoserine lactone hydrochloride (purity: 99%).

$^1$H NMR (300 MHz, DMSO) δ 8.83 (2H, brs), 4.46 (1H, t, J=8.8 Hz), 4.36-4.24 (2H, m), 2.61-2.51 (1H, m), 2.30 (1H, t, J=10.3 Hz)

$^1$H NMR (300 MHz, D$_2$O) δ 4.36 (1H, t, J=9.0 Hz), 4.29 (2H, q, J=9.0 Hz), 2.69-2.60 (1H, m), 2.36-2.21 (1H, m)

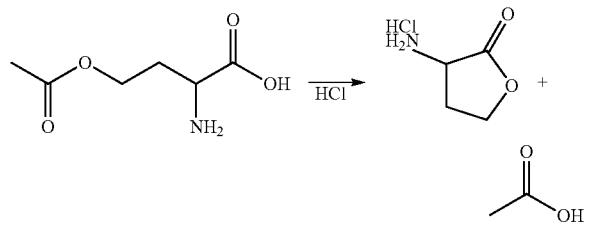

3-2) Synthesis of Homoserine Lactone and Succinic Acid from O-succinyl-L-homoserine 2 g (9.12 mmol) of O-succinyl-L-homoserine was dissolved in 10 ml (120 mmol, 13.2 equivalents) of concentrated hydrochloric acid, and the solution was allowed to react at 50° C. for 2 hours, and then cooled at room temperature for 3 hours. The precipitated solid was filtered, thereby obtaining 0.7 g (5.9 mmol) of succinic acid (SA) crystal (purity: 65%). The filtrate was concentrated and recrystallized with anhydrous ethanol to yield 1.2 g (8.72 mmol) of homoserine lactone hydrochloride (purity: 95%).

$^1$H NMR (300 MHz, DMSO) δ 8.83 (2H, brs), 4.46 (1H, t, J=8.8 Hz), 4.36-4.24 (2H, m), 2.61-2.51 (1H, m), 2.30 (1H, t, J=10.3 Hz): Homoserine lactone hydrochloride $^1$H NMR (300 MHz, D$_2$O) δ 4.36 (1H, t, J=9.0 Hz), 4.29 (2H, q, J=9.0 Hz), 2.69-2.60 (1H, m), 2.36-2.21 (1H, m): Homoserine lactone hydrochloride $^1$H NMR (300 MHz, D$_2$O) δ 2.47 (4H, s): Succinic acid

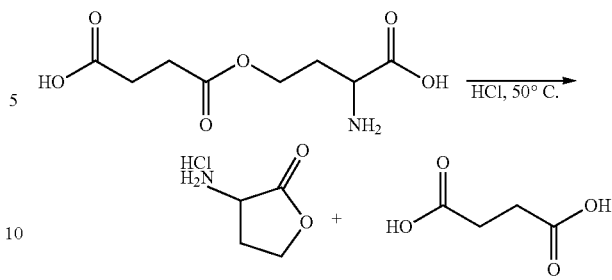

EXAMPLE 4

Synthesis of Gamma-butyrolactone from Homoserine Lactone

The homoserine lactone hydrochloride obtained in Example 3 was loaded in a reactor and hydrodenitrified with hydrogen gas under a pressure of 10-100 bar at 100~500° C. in the presence of a catalyst which supported on Pd, Pt, Ni or Co on C or silica, to produce gamma-butyrolactone.

EXAMPLE 5

Synthesis of Tetrahydrofuran from Gamma-butyrolactone

The gamma-butyrolactone obtained on Example 4 was dissolved in a solvent, and then etherified using a silane compound as a reducing agent at 60~80° C. in the presence of an indium bromide catalyst to produce tetrahydrofuran.

The $^1$H NMR spectrum was measured at 500 MHz using tetramethylsilane as an internal standard. The NMR spectrum was measured at 125 MHz using the central peak of chloroform (77.0 ppm) as an internal standard. High-resolution mass spectrometry was performed using NBA (3-nitrobenzylalcohol) as a matrix.

Under nitrogen atmosphere, gamma-butyrolactone (0.6 mmol), InBr$_3$ (10.6 mg, 0.0300 mmol) and triethylsilane (380 μL, 2.40 mmol) were sequentially added to 0.6 mL of distilled chloroform solution in a vial with a screw cap, and the vial was sealed with a cap having a PTFE film. When the reaction continued to stir at 60° C., the colorless solution changed to orange via yellow. The reaction was monitored by gas chromatography until the starting material, gamma-butyrolactone, was consumed. After completion of the reaction, water (3 mL) was added to the reaction product, and the orange suspension was continuously stirred until it became colorless. The aqueous phase was extracted with dichloromethane (15 mL), dried using anhydrous Na$_2$SO$_4$ and evaporated under reduced pressure. The crude product was purified by flash column chromatography (SiO$_2$/hexane:AcOEt=99:1) to yield tetrahydrofuran.

EXAMPLE 6

Synthesis of 2-Pyrrolidone from Gamma-butyrolactone

Using the gamma-butyrolactone obtained in Example 4,2-pyrrolidone was synthesized in an autoclave.

More specifically, 6.45 g (75 mmol) of gamma-butyrolactone and 10.9 g (1.1 equivalents, 82.5 mmol, 12 ml) of NH$_4$OH (26.5% in water) were placed in an autoclave, and 250 ml (0.3 M) of water was added thereto. The solution was allowed to react under a pressure of 53 bar at 270° C. for 1 hour.

After completion of the reaction, the starting material gamma-butyrolactone was not observed on TLC, and new spots were generated.

Water was removed from the reaction product, and the residue was extracted with CHCl₃. The organic layer was dried using MgSO₄. MgSO₄ was filtered out, and the filtrate was concentrated and analyzed by NMR. As a result, it could be seen that 6 g (70.5 mmol, 94%) of 2-pyrrolidone was produced.

¹H NMR (300 MHz, CDCl₃) δ 6.61 (1H, brs), 3.39 (2H, t, J=4.2 Hz), 2.28 (2H, t, J=5.6 Hz), 2.15~2.02 (2H, m)

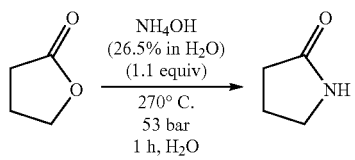 [SMILES: O=C1CCCO1 ; O=C1CCCN1]

EXAMPLE 7

Synthesis of N-methyl-2-pyrrolidone from Gamma-butyrolactone

Using the gamma-butyrolactone obtained in Example 4, N-methyl-2-pyrrolidone was synthesized under various reaction conditions as follows.

7-1) Synthesis of N-methyl-2-pyrrolidone from Gamma-butyrolactone Using Microwave Reactor N-methyl-2-pyrrolidone can be obtained by allowing gamma-butyrolactone and methylamine to react with each other in a water solvent at high temperature in a microwave reactor.

0.2 g (2.23 mmol) of gamma-butyrolactone and 0.36 g (2.0 equivalents, 4.64 mmol) of methylamine (40% in water) were placed in a 5 ml microwave reactor, and 5 ml (0.46 M) of water was added thereto. Then, the solution was allowed to react at 200° C. for 30 minutes. After completion of the reaction, the starting material gamma-butyrolactone was not observed on TLC, and new spots were generated. NMR analysis of the crude product showed that N-methyl-2-pyrrolidone was produced at a yield of 80%.

¹H NMR (300 MHz, CDCl₃) δ 3.32 (2H, t, J=5.3 Hz), 2.77 (3H, s), 2.30 (2H, t, J=6.2 Hz), 1.99-1.91 (2H, m)

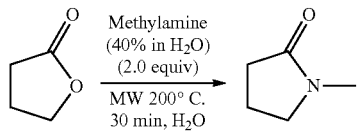

7-2) Synthesis a of N-methyl-2-pyrrolidone from Gamma-butyrolactone Using Parr Reactor 3.18 g (36.9 mmol) of gamma-butyrolactone and 6.44 g (2.0 equiv, 73.88 mmol, 7.23 ml) of methylamine (40% in water) were placed in a Parr reactor, and 100 ml (0.37 M) of water was added thereto. Then, the solution was allowed to react in the Parr reactor under a pressure of 15 bar at 220° C. for 4 hours.

After completion of the reaction, the starting material gamma-butyrolactone was not observed on TLC, and new spots were generated. NMR analysis of the crude product showed that N-methyl-2-pyrrolidone was produced at a yield of 50%.

¹H NMR (300 MHz, CDCl₃) δ 3.32 (2H, t, J=5.3 Hz), 2.77 (3H, s), 2.30 (2H, t, J=6.2 Hz), 1.99-1.91 (2H, m)

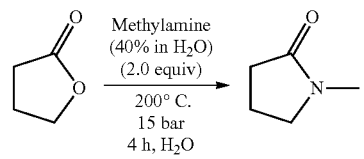

7-3) Synthesis B of N-methyl-2-pyrrolidone from Gamma-butyrolactone Using Parr Reactor 3.22 g (37.4 mmol) of gamma-butyrolactone and 2.9 g (1.0 equiv, 37.4 mmol, 3.3 ml) of methylamine (40% in water) were placed in a Parr reactor, and 100 ml (0.37 M) of water was added thereto. Then, the solution was allowed to react in the Parr reactor under a pressure of 15 bar at 220° C. for 4 hours.

After completion of the reaction, the starting material gamma-butyrolactone (GBL) was not observed on TLC, and new spots were generated. NMR analysis of the crude product showed that N-methyl-2-pyrrolidone was produced at a yield of 60%.

¹H NMR (300 MHz, CDCl₃) δ3.32 (2H, t, J=5.3 Hz), 2.77 (3H, s), 2.30 (2H, t, J=6.2 Hz), 1.99-1.91 (2H, m)

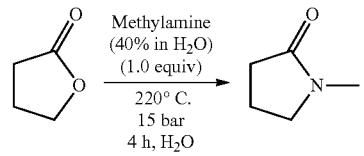

7-4) Synthesis of N-methyl-2-pyrrolidone from Gamma-butyrolactone Using Autoclave 6.45 g (75 mmol) of gamma-butyrolactone and 6.4 g (1.1 equiv, 82.5 mmol, 7.1 ml) of methylamine (40% in water) were placed in an autoclave, and 250 ml (0.3 M) of water was added thereto. Then, the solution was allowed to react under a pressure of 53.3 bar at 270° C. for 1 hour. After completion of the reaction, the starting material gamma-butyrolactone (GBL) was not observed on TLC, and new spots were generated. Water was removed from the reaction product, and the residue was extracted with CHCl₃. The organic layer was dried using MgSO₄. MgSO₄ was filtered out, and the filtrate was concentrated and analyzed by NMR. As a result, it could be seen that 6.92 g (69.8 mmol, 93%) of N-methyl-2-pyrrolidone was produced.

¹H NMR (300 MHz, CDCl₃) δ 3.32 (2H, t, J=5.3 Hz), 2.77 (3H, s), 2.30 (2H, t, J=6.2 Hz), 1.99-1.91 (2H, m)

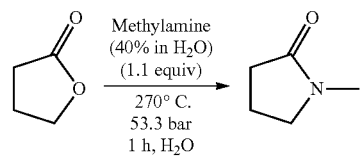

EXAMPLE 8

Preparation of N-vinyl-2-pyrrolidone from Gamma-butyrolactone

Using the gamma-butyrolactone obtained in Example 4, N-vinyl-2-pyrrolidone was produced by a first-stage reaction and a second stage reaction.

8-1) First-stage Reaction: Production of N-(2-hydroxyethyl)-2-pyrrolidone from Gamma-butyrolactone 356 g of ethanolamine and 100 g of water were placed in a 1-liter autoclave, which is kept under nitrogen atmosphere, at room temperature and 518 g of gamma-butyrolactone was added thereto with stirring. Then, the inside of the autoclave was pressurized with a 30 atm of nitrogen atmosphere and heated to 250° C., and the mixture was allowed to react for 2 hours.

Then, the reaction solution was cooled and analyzed by gas chromatography. The analysis showed that the yield of N-(2-hydroxyethyl)-2-pyrrolidone was 94 mol %.

The reaction solution was purified by distillation to yield N-(2-hydroxyethyl)-2-pyrrolidone.

8-2) Second-stage Reaction: Production of N-vinyl-2-pyrrolidone from N-(2-hydroethyl)-2-pyrrolidone To prepare as a catalyst to be used in the second-stage reaction, 7.76 g of cesium carbonate was dissolved in 250 g of water, and 30 g of silicon oxide was added thereto while the solution was heated to 90° C. and stirred. The mixture was dried at 120° C. for 20 hours. The resulting solid was crushed to size of 9-16 mesh, calcined in air at 500° C. for 2 hours, thereby preparing a catalyst having a composition of $Cs_1Si_{10}$ (expressed as atomic ratio excluding oxygen).

30 ml of the catalyst was charged into a stainless steel reaction tube having an inner diameter of 15 mm, and the reaction tube was placed in a reactor at 360° C. Raw material gas obtained by diluting N-(2-hydroxyethyl)-2-pyrrolidone in nitrogen to reach a partial pressure of 76 mmHg was supplied to the reaction tube at a space velocity of 200 $h^{-1}$ and allowed to react at atmospheric pressure. After 1 hour from the initiation of the reaction, gas discharged from the reactor was captured by methanol, and the gas chromatography analysis of the gas showed that the yield of N-vinyl-2-pyrrolidone was 87 mole %.

EXAMPLE 9

Production of 1,4-butanediol from Gamma-butyrolactone

The gamma-butyrolactone obtained in Example 4 was hydrogenated with hydrogen gas (50 bar) using 0.25 mol % of a ruthenium (Ru) catalyst and 1 mol % of an imidazole ligand in a THF solvent at 100° C. to yield 1,4-butanediol (Chem. Eur. J. 2012. 18, 9011-9018).

EXAMPLE 10

Production of Ethanol from Acetic Acid

Acetic acid produced as a byproduct in Example 3-1 was hydrogenated in the presence of a catalyst comprising a first metal, a second metal, a siliceous support and at least one support modifier to yield ethanol.

The catalyst used was a $SiO_2$—$CaSiO_3$—Pt—Sn catalyst prepared using Pt and Sn as the first and second metals, $SiO_2$ as the support and $CaSiO_2$ as the support modifier.

The hydrogenation reaction was performed by supplying hydrogen and acetic acid to the reactor at a pressure of 100 KPa at 250° C. and a gas hourly space velocity (GHSV) of 500 $hr^{-1}$ or higher. The molar ratio of hydrogen and acetic acid supplied was 11:1.

The hydrogenation reaction yielded 600 g or more of ethanol per kg of the catalyst.

EXAMPLE 11

Production of Ethylene from Ethanol

The ethanol obtained in Example 10 was allowed to react at 550° C. in the presence of a zeolite (ZSM-5) catalyst in a fixed-bed quartz reactor to produce ethylene (Catalysis, A: General, 2012, 162-167).

EXAMPLE 12

Production of Polyethylene from Ethylene

Ethylene gas obtained in Example 11 was allowed to react under nitrogen atmosphere (100 psi) at 50° C. for 20 minutes in the presence of a Ziegler-Natta catalyst to produce polyethylene (GB patent 1,406,282; 27 Jan. 1972).

EXAMPLE 13

Production of Monoethylene Glycol from Ethanol

The ethanol obtained in Example 10 was allowed to react with a $Na_2PtCl_4$ or $Na_2PtCl_6$ catalyst to produce monoethylene glycol (J. Am. Chem. Soc., 1994, 116, 998-1003).

EXAMPLE 14

Production of 1,4-butanediol from Succinic Acid

The succinic acid produced in Example 3-2 was hydrogenated in the presence of a catalyst comprising palladium, silver and rhenium metals on a carbon support to produce 1,4-butanediol.

14-1): Preparation of Catalyst

The catalyst to be used in hydrogenation was prepared in the following manner.

130.25 g of palladium nitrate solution (7.7% Pd), 16.5 g of silver nitrate and 41.5 g of perrhenic acid (52.6%, Re) were placed in a 250-cc flask, and acetonitrile was added thereto. The mixture was stirred to dissolve entirely. The solution had a weight of 296.2 g.

Then, 276.5 g of 1.5 mm ACL40 (manufactured by CECA S.A. (France; Marketed by Atochem North America Inc.) as a carbon support was impregnated with 286.4 g of the Pd/Ag/Re solution and allowed to stand for 5.75 hours. Then, the mixture was dried in an oven at 120° C. overnight to yield a catalyst comprising 3.3 wt % Pd, 3.2 wt % Ag and 6.6 wt % Re on the carbon support (ACL 40).

14-2) Production of 1,4-butanediol

Succinic acid was hydrogenated with hydrogen in water in the presence of the catalyst comprising palladium, silver and rhenium metals on the carbon support under pressure of 2500 psig at 160° C., a GHSV of 2760 hr$^{-1}$ and a LHSV of 0.55 hr$^{-1}$ to yield 1,4-butanediol.

EXAMPLE 15

Production of Gamma-butyrolactone and Tetrahydrofuran from Succinic Acid

The succinic acid produced in Example 3-2 was treated with a commercial MCM-41 and then hydrogenated in the presence of a catalyst comprising platinum, Palladium and ruthenium metals to produce gamma-butyrolactone and tetrahydrofuran.

15-1) Preparation of Catalyst

The catalysts used in hydrogenation were all prepared by a wet impregnation method.

The precise metal precursors used were tetraammineplatinum (II) nitrate, palladium (II) nitrate solution and ruthenium (III) chloride hydrate. 15 wt % of each of the precursors was placed in a 250-ml round bottom flask together with 1 g of pretreated commercial MCM-41 support (Sigma-Aldrich), and then an excess amount of water or acetone solvent was added thereto, and the pressure of the flask was reduced using a rotary vacuum pump, thereby preparing a catalyst.

The prepared catalyst was dried overnight in an oven at about 120° C. Before the catalytic reaction, the catalyst was reduced by hydrogen at 450° C. for 5 hours.

15-2) Production of Gamma-butyrolactone and Tetrahydrofuran

In a batch reactor, 5 g of the succinic acid produced in Example 3-2) and to 3 g of the catalyst prepared in Example 15-1) were added to 50 ml of 1,4-dioxane solvent to produce gamma-butyrolactone and tetrahydrofuran. Specifically, hydrogen was added to the reactor until a reaction pressure reached to 1467 psi, followed by a reaction for 10 hours, thereby producing gamma-butyrolactone and tetrahydrofuran. The results of the reaction are shown in Table 6 below.

TABLE 6

Production of gamma-butyrolactone and tetrahydrofuran

| catalyst | Conversation rate (mol %) | yield (mol %) GBL | THF |
|---|---|---|---|
| Pt/MCM-41 | 52.6 | 23.1 | 14.4 |
| Pd/MCM-41 | 50.7 | 23.9 | 15.1 |
| Ru/MCM-41 | 62.5 | 30.3 | 18.8 |

EXAMPLE 16

Production of Gamma-butyrolactone from 1,4-butanediol

The 1,4-butanediol produced in Example 14 was dehydrogenated in the presence of a copper-zinc-based catalyst to yield gamma-bytyrolactone.

16-1) Preparation of Catalyst

In a flask, 195 g of copper acetate, 20 g of zinc nitrate, 101 g of aluminum nitrate and 36 g of zirconyl nitrate were dissolved in water. To the solution, a solution of 124 g of sodium hydroxide in 1 L of water was added to form a precipitate by co-precipitation. The precipitate was washed with water, dried, and then calcined at 500° C. to yield a catalyst precursor. 25 g of the catalyst precursor was charged into a catalyst bed (inner diameter: 17 mm; length: about 100 mm) of a fixed-bed flow reactor with gas-phase reactions under atmospheric pressure and reduced with hydrogen (diluted with nitrogen) as a reducing agent at 200° C. for 8 hours to establish a Cu—ZnO—Al$_2$O$_3$—ZrO$_3$ catalyst layer for production of gamma-butyrolactone in the reactor.

16-2) Production of Gamma-butyrolactone

The carrier gas, nitrogen, was flowed downward from the upper part of the fixed-bed flow reactor having the Cu—ZnO—Al$_2$O$_3$—ZrO$_3$ catalyst layer at a flow rate of 30 ml/min under atmospheric pressure. 1,4-butanediol was supplied together with the nitrogen gas, vaporized in the vaporizing layer and supplied to the catalyst layer. Herein, the temperature of the vaporizing layer and the catalyst layer was 240° C. Upon the increase of LHSV (liquid hourly space velocity) to 0.5 h$^{-1}$ of 1,4-butanediol, the maximum yield of gamma-butyrolactone were 97.9%.

EXAMPLE 17

Production of Tetrahydrofuran from 1,4-butanediol

The 1,4-butanediol produced in Example 9 or Example 14 was dehydrated in the presence of a tungstic oxide catalyst supported on an alumina carrier to produce tetrahydrofuran.

Specifically, 150 g of 1,4-butanediol and 15.0 g of tungstic acid (H$_2$WO$_4$) were charged into an autoclave and heated under hydrogen pressure of 1000 psi at 200° C. with stirring at 1000 rpm for 2 hours to produce 112 g of tetrahydrofuran.

---

What is claimed is:

1. A method for producing bio-based homoserine lactone and bio-based organic acid, comprising hydrolysis of O-acyl homoserine produced by a microorganism in the presence of a hydrochloric acid catalyst.

2. The method according to claim 1, wherein the O-acyl homoserine includes O-acetyl-L-homoserine or O-succinyl-L-homoserine.

3. The method according to claim 1, wherein the bio-based organic acid includes acetic acid or succinic acid.

4. The method according to claim 1, wherein the O-acyl homoserine is produced by the microorganism whose cystathionine gamma synthase, O-succinylhomoserine sulfhydrylase or O-acetylhomoserine sulfhydrylase activity was removed or weakened as compared to the endogenous form thereof.

5. The method according to claim 2, wherein the O-acetyl-L-homoserine is produced by the microorganism whose homoserine O-acetyl transferase activity was enhanced as compared to the endogenous form thereof.

6. The method according to claim 2, wherein the O-succinyl-L-homoserine is produced by the microorganism whose O-succinyl transferase activity was enhanced as compared to the endogenous form thereof.

7. A method for producing gamma-butyrolactone, comprising the steps of:
hydrolyzing O-acyl homoserine produced by a microorganism in the presence of a hydrochloric acid catalyst to produce bio-based homoserine lactone and bio-based organic acid; and
deaminating the homoserine lactone by hydrodenitrification in the presence of a metal catalyst and hydrogen gas to produce gamma-butyrolactone.

8. The method according to claim 7, wherein the method further comprises the steps of:
etherifying the gamma-butyrolactone in the presence of an indium bromide catalyst and a silane compound to produce tetrahydrofuran.

9. The method according to claim 7, wherein the method further comprises the steps of:
producing 2-pyrrolidone from the gamma-butyrolactone in the presence of an aqueous ammonia solution.

10. The method according to claim 7, wherein the method further comprises the steps of:
producing N-methyl-2-pyrrolidone from the gamma-butyrolactone in the presence of liquid methylamine.

11. The method according to claim 7, wherein the method further comprises the steps of:
dehydrating the gamma-butyrolactone in the presence of liquid ethyl alcohol amine to produce N-(2-hydroxyethyl)-2-pyrrolidone (first-stage reaction); and
dehydrating the N-(2-hydroxyethyl)-2-pyrrolidone in the presence of an oxide catalyst containing an alkali metal or an alkaline earth metal and silicon to produce N-vinyl-2-pyrrolidone (second-stage reaction).

12. The method according to claim 7, wherein the method further comprises the steps of:
hydrogenating the gamma-butyrolactone with an imidazole ligand in the presence of a ruthenium catalyst to produce 1,4-butanediol.

13. A method for producing ethanol, comprising the steps of:
hydrolyzing O-acetyl-L-homoserine produced by a microorganism in the presence of a hydrochloric acid catalyst to produce bio-based homoserine lactone and bio-based acetic acid; and hydrogenating the acetic acid in the presence of a catalyst comprising a first metal, a siliceous support and at least one support modifier to produce ethanol.

14. The method according to claim 13, wherein the method further comprises the steps of:
dehydrating the ethanol in the presence of a zeolite (ZSM-5) catalyst to produce ethylene.

15. The method according to claim 13, wherein the method further comprises the steps of:
dehydrating the ethanol in the presence of a catalyst to produce ethylene; and
polymerizing the ethylene in the presence of a Ziegler-Natta catalyst to produce polyethylene.

16. The method according to claim 13, wherein the method further comprises the steps of:
hydrolyzing the ethanol in the presence of a platinum-based catalyst to produce monoethylene glycol.

17. A method for producing 1,4-butanediol, comprising the steps of:
hydrolyzing O-succinyl-L-homoserine produced by a microorganism in the presence of a hydrochloric acid catalyst to produce bio-based homoserine lactone and bio-based succinic acid; and
hydrogenating the succinic acid in the presence of a metal catalyst on a carbon support to produce 1,4-butanediol and tetrahydrofuran.

18. The method according to claim 17, wherein the method further comprises the step of:
dehydrogenating the 1,4-butanediol in the presence of a copper-zinc-based catalyst to produce gamma-butyrolactone.

19. A method for producing gamma-butyrolactone and tetrahydrofuran, comprising the steps of:
hydrolyzing O-succinyl-L-homoserine produced by a microorganism in the presence of a hydrochloric acid catalyst to produce bio-based homoserine lactone and bio-based succinic acid;
treating the succinic acid with MCM-41; and
hydrogenating the treated succinic acid in the presence of a noble metal catalyst selected from platinum, palladium and ruthenium to produce gamma-butyrolactone and tetrahydrofuran.

20. The method according to claim 17, wherein the method further comprises the steps of:
dehydrating the 1,4-butanediol in the presence of a catalyst selected from inorganic acid, tungstic oxide and iron phosphate to produce tetrahydrofuran.

* * * * *